United States Patent [19]
Gunn et al.

[11] Patent Number: 4,561,001
[45] Date of Patent: Dec. 24, 1985

[54] ELECTROCHROMIC MARKING SYSTEMS

[75] Inventors: Michael B. Gunn; William M. Hung, both of Cincinnati, Ohio

[73] Assignee: The Hilton-Davis Chemical Co., Cincinnati, Ohio

[21] Appl. No.: 636,460

[22] Filed: Jul. 31, 1984

[51] Int. Cl.$^4$ .............................................. B41M 5/20
[52] U.S. Cl. ...................................... 346/218; 204/2; 346/217; 427/151
[58] Field of Search ................ 346/217, 218; 427/150, 427/151; 204/2; 544/3

[56] References Cited

U.S. PATENT DOCUMENTS

| | | | |
|---|---|---|---|
| 2,909,520 | 10/1959 | Buc | 260/243 |
| 3,873,340 | 3/1975 | Miyazawa et al. | 346/218 |
| 3,900,217 | 8/1975 | Hayashi et al. | 346/218 |
| 4,309,255 | 1/1982 | Gendler et al. | 204/2 |

FOREIGN PATENT DOCUMENTS

| | | | |
|---|---|---|---|
| 46-35704 | 10/1971 | Japan | 346/218 |
| 51-81629 | 7/1976 | Japan | 346/218 |
| 55-040798 | 3/1980 | Japan | 346/218 |
| 6104094 | 8/1981 | Japan | 346/218 |

OTHER PUBLICATIONS

Mariga & Oda "Color Reaction of Some Derivatives of Aminophthalide and Acylleucomethylene Blue Derivatives"–Kogyo Kagaku Zasshi 67 (7) 1050-4 (1964) (C.A. 62 2852b).

Smets & Simionescu "Polymer Induced Aggregation of Dye Molecules" Makromolecular Chemistry, 1977 198(9), 2719-23 (C.A. 87 186052t).

Primary Examiner—Bruce H. Hess
Attorney, Agent, or Firm—Terrence E. Miesle; Thomas L. Johnson; B. Woodrow Wyatt

[57] ABSTRACT 3-(N-$R^2$-N-Acylamino)-7-(N-$R^3$-N-$R^4$-amino)-10-acyl-phenothiazines and phenoxazines useful as color formers, particularly in electrochromic recording systems, are prepared by the interaction of the corresponding 3-(N-$R^2$-amino)-7-(N-$R^3$-N-$R^4$-amino)phenothiazinium or phenoxazinium halide with a reducing agent to obtain the corresponding leuco compound and subsequently interacting the leuco compound with at least two molecular proportions of an acylating agent.

8 Claims, No Drawings

ELECTROCHROMIC MARKING SYSTEMS

BACKGROUND OF THE INVENTION (a) Field of the Invention

This invention relates to novel compounds classified in the field of organic chemistry as phenothiazines and phenoxazines, useful as color-forming substances, particularly in the art of electrochromic recording; to electrochromic recording systems containing said compounds; and to processes for preparing said compounds.

(b) Information Disclosure Statement

Several classes of organic compounds of widely diverse structural types are known to be useful as colorless precursors for electrochromic recording. Among the more important classes, there may be named leuco-type dyestuffs such as: phthalides, for example, crystal violet lactone, Malachite green lactone; fluorans, for example, 3-diethylamino-5,7-dimethylfluoran; and indolinobenzospiropyrans, for example, 1,3,3-trimethyl-6'-chloro-8'-methoxyindolinobenzospiropyrans. Also utilized as colorless precursors for electrochromic recording, either alone or in admixture with the leuco compounds indicated above, are substances known as redox indicators. The redox indicator which becomes colored in situ in the electrochromic recording process also is generally a leuco compound. Among the types of compounds which are applicable as redox indicators are phenothiazines, for example, leuco methylene blue and benzoyl leuco methylene blue. Other specific indicators are Leucoethyl Nile Blue, Leucomethyl Capyrl Blue and Leucosafranine T. Typical of the many such electrochromic recording systems taught in the prior art are those described in U.S. Pat. Nos. 3,726,769, 3,871,972, 3,864,684, 4,017,366, 4,133,933, and Reissue Patent Re. 29,427 which issued Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. Basically, a sheet of paper is coated or treated on one or both sides with a coating formulation containing at least one colorless color-forming (leuco) compound. Electrical current is then selectively applied to the coated side of the paper by some means, for example, a stylus or a printing head to which an electrical potential can be applied. The application of the current causes an electrochromic reaction involving the leuco compound to produce a visible image corresponding to the design traced by the stylus or that of the printing head.

The following items to date appear to constitute the most relevant prior art with regard to the instant invention.

U.S. Pat. No. 2,909,520, issued Oct. 20, 1959, discloses compounds having the formula

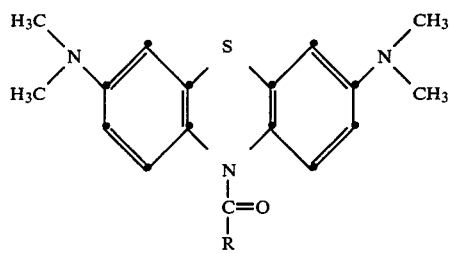

in which R is a phenyl or naphthyl moiety substituted with one or more of the following moieties: alkyl, alkoxy, halo, nitro, haloalkyl, alkoxycabonyl, phenyl, and phenylalkoxy. These compounds are disclosed as being useful as blue color formers in carbonless carbon papers, i.e., carbonless duplicating systems.

Mariga and Oda in Kogyo Kagaku Zasshi 67 (7), 1050-4 (1964) (C.A. 62 2852b) describe the preparation and properties of acylated methylene blue having the structural formula

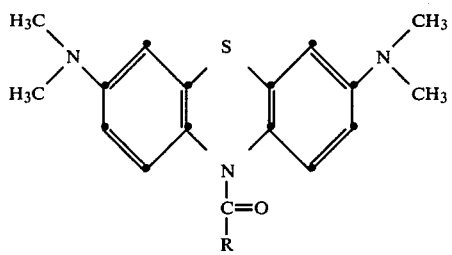

in which R represents an alkyl or a substituted phenyl moiety. The compounds are disclosed as being useful in pressure-sensitive carbonless duplicating systems.

U.S. Pat. No. 4,309,255, issued Jan. 5, 1982, discloses and claims a phenothiazine having the structural formula

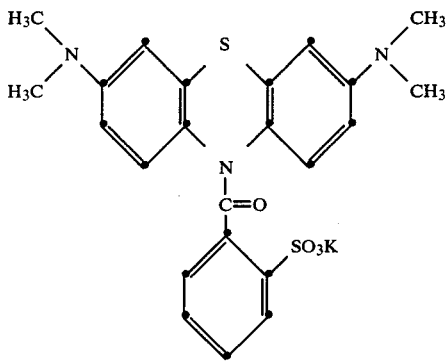

which is disclosed as being useful as a blue color former in electrochromic recording paper.

Smets and Simionescu in Makromolecular Chemistry 1977 178(9), 2719-23 (C.A. 87 186052t) disclose as a monomer for a colored polymer N-acryloyl-N,N',N'-trimethylthionine having the formula

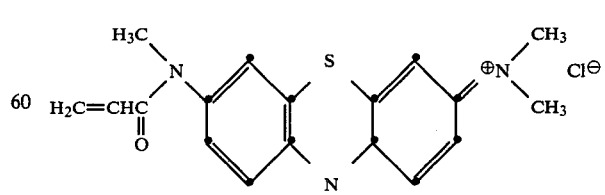

Japanese Patent Publication No. 80,040,798, published Mar. 22, 1980, discloses thionines having the structural formula

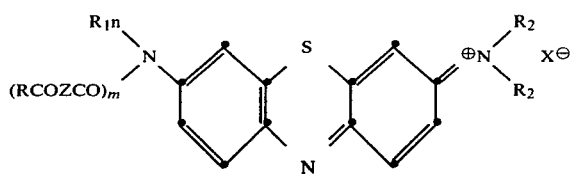

in which $R_1$ and $R_2$ represent hydrogen or methyl; R and X represent halogen; Z represents $(CH_2)_3$ to 12; n represents zero or one; m represents one or two; and m+n equals two. The compounds are disclosed as being monomers for reaction with polyethyleneimine to obtain a green-blue solid which is swellable by water and N,N-dimethylformamide.

SUMMARY OF THE INVENTION

In its composition of matter aspect, the invention relates to certain 3-(N-$R^2$-N-acylamino)-7-(N-$R^3$-N-$R^4$-amino)-10-acyl-phenothiazines and phenoxazines useful as colorless precursors in electrochromic recording systems.

The present invention provides in its article of manufacture aspect, a substrate for use in electrochromic recording systems comprising a support sheet containing as a color-forming substance 3-(N-$R^2$-N-acylamino)-7-(N-$R^3$-N-$R^4$-amino)-10-acyl-phenothiazines and phenoxazines.

In its process aspect, the invention relates to a process for producing 3-(N-$R^2$-N-acylamino)-7-(N-$R^3$-N-$R^4$-amino)-10-acyl-phenothiazines and phenoxazines which comprises interacting the corresponding 3-(N-$R^2$-amino)-7-(N-$R^3$-N-$R^4$-amino)phenothiazinium or phenoxazinium halide with a reducing agent to obtain the corresponding leuco compound and subsequently interacting the leuco compound with at least two molecular proportions of an acylating agent.

DETAILED DESCRIPTION INCLUSIVE OF THE PREFERRED EMBODIMENTS

More specifically, this invention in its composition of matter aspect resides in the novel compounds having the structural formula

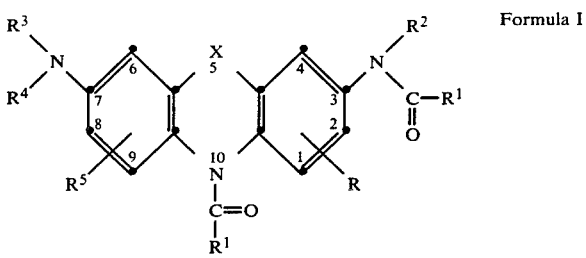

Formula I wherein R and $R^5$ independently represent non-tertiary $C_1$ to $C_4$ alkyl, non-tertiary $C_1$ to $C_4$ alkoxy, halogen or nitro; $R^1$ represents hydrogen, non-tertiary $C_1$ to $C_{12}$ alkyl, $C_4$ to $C_8$ cycloalkyl, non-tertiary $C_1$ to $C_{12}$ alkyl substituted by halogen, non-tertiary $C_1$ to $C_4$ alkoxy or non-tertiary $C_1$ to $C_4$ alkoxycarbonyl, phenyl, phenyl substituted by one to three of non-tertiary $C_1$ to $C_4$ alkyl, non-tertiary $C_1$ to $C_4$ alkoxy, nitro, halo, phenyl, cyano or trihalomethyl; $R^2$ represents hydrogen, non-tertiary $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; $R^3$ and $R^4$ represent hydrogen, non-tertiary $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; and X represents S or O.

Particular embodiments within the ambit of the composition of matter aspect are the novel 1/2-R-3-[N($R^1$-CO)-N-$R^2$-amino]-7-(N-$R^3$-N-$R^4$-amino)-8/9-$R^5$-10-($R^1$-CO)-phenothiazines of Formula I wherein X is S having the formula

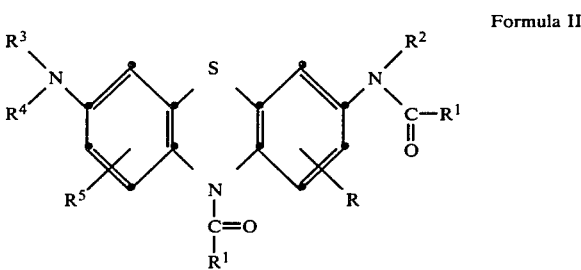

Formula II in which R, $R^1$, $R^2$, $R^3$, $R^4$ and $R^5$ have the same respective meanings given in Formula I.

Other particular embodiments with the ambit of the composition of matter aspect are the novel 1/2-R-3-[N-($R^1$-CO)-N-$R^2$-amino]-7-(N-$R^3$-N-$R^4$-amino)-8/9-$R^5$-10-($R^1$-CO)-phenoxazines of Formula I wherein X is O having the structural formula

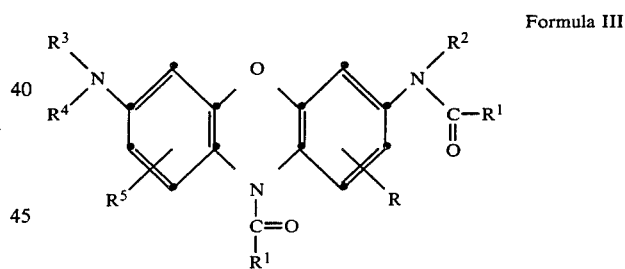

Formula III in which R, $R^1$, $R^2$, $R^3$, $R^4$ and $R^5$ have the same respective meanings given in Formula I.

In its process aspect, the invention sought to be patented resides in the process for preparing a compound according to Formula I having the structural formula

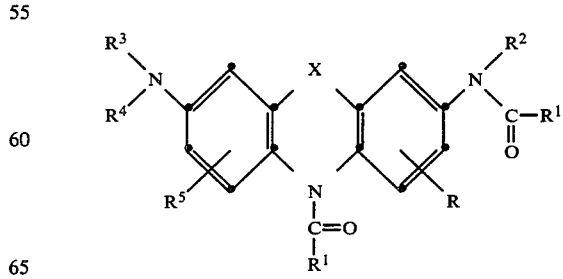

which comprises in the first step interacting a compound having the structural formula

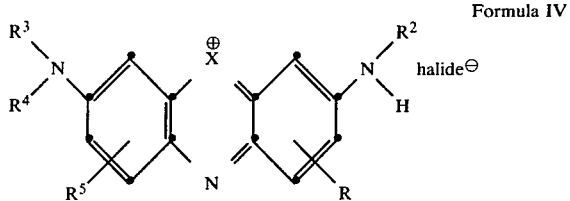

Formula IV with a reducing agent to obtain the corresponding leuco compound having the structural formula

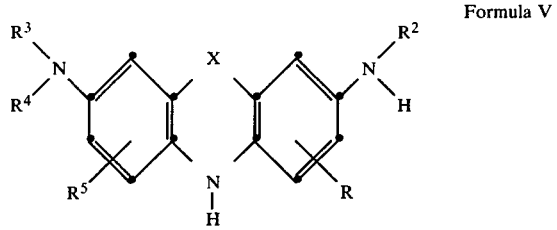

Formula V and in a second step, interacting the leuco compound with at least two molecular proportions of an acylating agent having the structural formula $R^1—CO—Z$     Formula VI in which Z represents halo or $R^1COO$ and R, $R^1$, $R^2$, $R^3$, $R^4$ and $R^5$ have the same respective meanings given in Formula I.

In its article of manufacture aspect, the invention sought to be patented resides in a substrate for use in electrochromic recording comprising a support sheet containing as a color-forming substance a phenothiazine or phenoxazine having the structure of Formula I.

A particular embodiment within the ambit of the article of manufacture aspect in the substrate for use in electrochromic recording comprising a support sheet containing as a color-forming substance a 1/2-R-3-[N-($R^1$-CO)-N-$R^2$-amino]-7-(N-$R^3$-N-$R^4$-amino)-8/9-$R^5$-10-($R^1$-CO)-phenothiazine of Formula II wherein R, $R^1$, $R^2$, $R^3$, $R^4$ and $R^5$ have the same respective meanings given in Formula II.

In a second particular embodiment within the ambit of its article of manufacture aspect is the substrate for use in electrochromic recording comprising a support sheet containing as a color-forming substance a 1/2-R-3-[N-($R^1$-CO)-N-$R^2$-amino]-7-(N-$R^3$-N-$R^4$-amino)-8/9-$R^5$-10-($R^1$-CO)-phenoxazine of Formula III wherein R, $R^1$, $R^2$, $R^3$, $R^4$ and $R^5$ have the same respective meanings given in Formula III.

As used herein the terms "non-tertiary $C_1$ to $C_4$ alkyl" and "non-tertiary $C_1$ to $C_{12}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl and the like.

The term "non-tertiary $C_1$ to $C_4$ alkoxy" includes saturated acyclic, straight or branched-chain groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

As used herein the term "$C_4$ to $C_8$ cycloalkyl" denotes saturated monovalent cyclic aliphatic hydrocarbon radicals including cyclobutyl, cyclopentyl, cyclohexyl, cycloheptyl, cyclooctyl and the like.

The phenothiazinium and phenoxazinium dyes which are used as intermediates or starting materials for the compounds of Formula I are generally known dyestuffs readily prepared by procedures well known in the dyestuff art. Four references to the preparation of the phenothiazine and phenoxazine dyestuffs are: (a) Journal of the Society of Dyers and Colourists 4, 39 (1888); (b) Liebig's Annalen der Chemie 251, 1 (1889); (c) Chemische Berichte 25, 3128 (1892); (d) FIAT Final Report No. 1313 and PB Report 85172, Vol. II, p. 372.

The acylating agents of Formula VI may be either aliphatic acid anhydrides ($Z=R^1COO$) or acid halides ($Z=$halo, preferably chloro), both of which constitute well known classes of compounds many of which are commercially available or are readily obtained by conventional synthesis well known in the art. The following list exemplifies aliphatic acid anhydrides and acid halides useful in carrying out the processes of this invention. Acetic anhydride, chloroacetic anhydride, dichloroacetic anhydride, trifluoroacetic anhydride, propionic anhydride, butyric anhydride, isobutyric anhydride, valeric anhydride, hexanoic anhydride, hepanoic anhydride, acetyl bromide, acetyl chloride, acetyl fluoride, bromoacetyl bromide, bromoacetyl chloride, chloroacetyl chloride, methoxyacetyl chloride, propionyl chloride, 2-bromopropionyl chloride, 3-bromopropionyl chloride, 2-chloropropionyl chloride, 3-chloropropionyl chloride, butyryl chloride, 4-chlorobutyryl chloride, 2-ethylbutyryl chloride, isobutyryl chloride, valeryl chloride, 5-chlorovaleryl chloride, isovaleryl chloride, 4-methylvaleryl chloride, hexanoyl chloride, 6-bromohexanoyl chloride, heptanoyl chloride, octanoyl chloride, nonanoyl chloride, decanoyl chloride, 10-undecanoyl chloride, palmitoyl chloride, myristoyl chloride, lauroyl chloride, cyclopropyl carboxylic acid chloride, cyclobutane carboxylic acid chloride, cyclohexyl carboxylic acid chloride, m-anisoyl chloride, p-anisoyl chloride, benzoyl bromide, benzoyl chloride, benzoyl fluoride, 4-biphenylcarbonyl chloride, 2-bromobenzoyl chloride, 4-bromobenzoyl chloride, 4-butoxybenzoyl chloride, 4-butylbenzoyl chloride, 2-chlorobenzoyl chloride, 3-chlorobenzoyl chloride, 4-chlorobenzoyl chloride, 4-cyanobenzoyl chloride, 2,4-dichlorobenzoyl chloride, 2,6-dichlorobenzoyl chloride, 3,4-dichlorobenzoyl chloride, 3,5-dimethoxybenzoyl chloride, 3,4-dimethoxybenzoyl chloride, 3,5-dinitrobenzoyl chloride, 2-fluorobenzoyl chloride, 3-fluorobenzoyl chloride, 4-fluorobenzoyl chloride, 3-nitrobenzoyl chloride, 4-nitrobenzoyl chloride, 2-methoxybenzoyl chloride, 3-methylbenzoyl chloride, 4-methylbenzoyl chloride, 2-iodobenzyl chloride, 4-iodobenzoyl chloride and 4-trifluoromethylbenzoyl chloride.

The compounds of Formula I hereinabove are essentially colorless in the depicted form. When contacted with an electric current from an applied voltage stylus of the type ordinarily employed in electrochromic recording systems, the compounds of Formula I develop green, green-black, black and blue-black-colored images. These developed images are very insensitive to light, that is, once the color is developed, it remains unchanged when subjected to light exposure. The developed images also possess excellent xerographic reproducibility.

The compounds of this invention may be incorporated in any of the commercially-accepted systems known in the electrochromic recording art. Typical techniques for the application of the color formers to paper are well known and are described in numerous patents, for example, U.S. Pat. Nos. Re. 29,427; 3,726,769; 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionally in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkaline metal or alkaline earth metal salt, for example, potassium chloride, calcium chloride, sodium chloride, sodium bromide, potassium bromide, potassium nitrate or sodium sulfate immediately prior to the printing with the applied voltage stylus. For a quick qualitative test, it has been determined that the color-forming component can be dissolved in a suitable volatile organic solvent, coated on paper and the coated paper dried to obtain a paper sheet coated with the color-forming component. This coated sheet can then be wet with a conductive salt solution and an image traced with an applied voltage stylus to develop the colored image.

The compounds of Formula I can be used alone as color-forming components in electrochromic recording paper or can be used in admixture with one or more other color-forming compounds from the classes consisting of phthalides, for example, Crystal Violet Lactone; fluorans, for example, 3-diethylamino-5,7-dimethylfluoran; redox indicators, for example, phenothiazines such as benzoyl leuco methylene blue and various other types of color-forming components currently employed in commercially-accepted electrochromic recording systems.

The best mode contemplated by the inventors of carrying out this invention will now be described so as to enable any person skilled in the art to which it pertains to make and use the same.

In accordance with the aforementioned process aspects of this invention, the compounds of Formula I are obtained by reacting one molecular proportion of a leuco compound of Formula V with at least two molecular proportions of an acylating agent of Formula VI. When using an anhydride as the acylating agent, the reaction is conveniently carried out in an excess of the acylating agent which is utilized as both the reaction medium and as the reactant. Optionally a small amount of an organic base, for example, pyridine may be used as a catalyst. The reaction is conveniently carried out at a temperature in the range of 90° C. to reflux of the mixture for periods of approximately thirty minutes to approximately four hours. The compounds of Formula I thus obtained are isolated by pouring the reaction mixture into ice water and extracting the desired products into a suitable water immiscible organic liquid, for example, toluene. The organic liquid layer containing the product is subsequently washed with water to remove inorganic salts and water-soluble organics and then treated with decolorizing charcoal, if desired. The resulting organic liquid solution of the product is then concentrated by conventional means such as evaporation or distillation.

Alternatively, the compounds of Formula I can be obtained also by reacting approximately one molecular proportion of a leuco compound of Formula V with about two molecular proportions of an acyl halide of Formula VI (Z=halo). A solution of the leuco compound dissolved in an organic liquid is cooled to a temperature in the range of 60° to 80° C. and disodium phosphate and acyl halide, dissolved in the same organic liquid, is added. The reaction is conveniently carried out at the reflux temperature of the mixture for periods of approximately fifteen minutes to approximately nineteen hours. Water and additional disodium phosphate are added to the reaction mixture and the resulting mixture is heated at reflux temperature for a period of approximately thirty minutes to approximately one hour. The organic liquid solution containing the desired product is separated from the water layer, washed with water and concentrated by conventional means such as evaporation or distillation. The isolated product can be purified by conventional means such as recrystallization or reslurrying with a suitable organic liquid and then collected by filtration. Purification can also be effected by column chromatography. The material to be purified is dissolved in a suitable organic liquid and the solution is passed through a chromatography column which has been packed with a suitable substrate, for example, silica gel, cellulose, alumina and the like. Numerous fractions are collected and analyzed to determine fraction(s) containing the desired product. The fraction(s) which contain the desired product are then combined (if more than one) and concentrated to obtain the product. The leuco compound of Formula V is conveniently prepared by reducing the corresponding phenothiazinium or phenoxazinium halide dyestuff of Formula IV with a reducing agent, for example, zinc dust. This reaction is conveniently carried out in an excess of the alkanoic anhydride acylating agent thus resulting in no need for an inert organic liquid reaction medium. Alternatively, the leuco compound of Formula V is conveniently prepared by reducing the corresponding phenolthiazinium halide or phenoxazinium halide of Formula IV with a reducing agent, for example, an alkaline hydrosulfite. The reaction in which the leuco compound is prepared is conveniently carried out in a mixture of water and a suitable water immiscible organic liquid, for example, toluene or xylene in an inert atmosphere, for example, nitrogen. The reaction is carried out in the presence of an alkaline substance, for example, sodium carbonate or disodium phosphate using, as the reducing agent, an alkali hydrosulfite, for example, sodium hydrosulfite. The reaction is conveniently carried out at ambient temperature for a period of approximately fifteen minutes to approximately two hours. The organic liquid solution which contains the leuco compound is separated from the water layer. Additional alkali hydrosulfite is added to the organic liquid solution and the resulting mixture is azeotroped to remove the remaining trace of water. The resulting solution can be used directly in the acylating step of the process.

The molecular structures of the compounds were assigned on the basis of the modes of synthesis and a study of their infrared, nuclear magnetic resonance and mass spectra.

The following examples will further illustrate the invention without, however, limiting it thereto.

EXAMPLE 1

A mixture of 10.0 g of Azure B (Aldrich) 7-(dimethylamino)-3-(methylamino)phenothiazin-5-ium chloride, 75.0 ml of 90 percent formic acid, 5.0 g of zinc dust and 5.0 ml of pyridine was maintained at approximately 90° C. for approximately three hours. The reaction mixture was cooled to room temperature and filtered, saving the filtrate. The filter cake was washed twice, each time with 50.0 ml of acetone, and the washes combined with the filtrate. The combined filtrate and washes was poured into ice water with stirring. The resulting solution was extracted with toluene. The toluene solution was separated, treated with decolorizing carbon, filtered and the resulting solution was evaporated under reduced pressure to obtain a gummy residue. The gummy residue was titurated with a 1:1 (V:V) mixture of isopropyl alcohol and hexane. The solid which formed was collected by filtration and dried to obtain 0.14 g of 7-(dimethylamino)-3-(N-formyl-N-methylamino)-10-formylphenothiazine (Formula II: $R=R^1=R^5=H$; $R^2=R^3=R^4=CH_3$), an off-white-colored powder which melted at 139° to 143° C. A significant infrared maximum appeared at 1685 cm$^{-1}$ (C=O;s). A paper treated with an ink formulation of the product produced a black-colored image when traced with an applied voltage stylus.

EXAMPLE 2

A mixture of 9.0 g of 7-(dimethylamino)-3-methylamino-2-methyl-phenothiazin-5-ium chloride, 150.0 ml of acetic anhydride and 10.0 g of zinc dust was maintained at reflux temperature for approximately four hours. After the reaction mixture was cooled to ambient temperature, it was poured into ice water with stirring and toluene was added. After stirring for approximately one-half hour, the toluene layer was separated and washed twice, once with tap water and once with saturated aqueous sodium chloride solution. The toluene was then removed at reduced pressure. The residue which remained was dissolved in ethyl acetate and separated into various components by subjecting the solution to column chromatography using silica gel as the substrate. The fourth and fifth fractions were combined and the ethyl acetate evaporated to obtain 3.79 g of 7-(dimethylamino)-3-(N-acetyl-N-methylamino)-2-methyl-10-acetylphenothiazine (Formula II: $R=2-CH_3$; $R^1=R^2=R^3=R^4=CH_3$; $R^5=H$), a white-colored solid which melted over the range of 148° to 161° C. A significant infrared maximum appeared at 1665 cm$^{-1}$ (C=O;s). A significant maxima appeared in the mass spectrum at 369 (M+) and 326 (M+—CH$_3$CO). Paper treated with an ink formulation of the product produced a black-colored image when traced with an applied voltage stylus.

EXAMPLE 3

The reaction vessel was purged of residual air with nitrogen and, while maintaining a nitrogen atmosphere, there was placed in the vessel, 10.0 g of Azure B (Aldrich) 7-(dimethylamino)-3-(methylamino)-phenothiazin-5-ium chloride, 500.0 ml of water and 500.0 ml of toluene. With stirring, there was added to the resulting mixture, 10.0 g of sodium carbonate and 15.0 g of sodium hydrosulfite. The resultant mixture was stirred for approximately fifteen minutes at ambient temperature and the water layer was separated and discarded. To the toluene layer, 10.0 g of sodium hydrosulfite was added and the resulting mixture was heated at reflux temperature until all of the water was azeotroped from it. After the mixture dried, it was cooled to approximately 70° C. and 15.0 g of disodium phosphate was added. To this mixture, there was added a solution of 20.0 ml of 4-methylbenzoyl chloride dissolved in 30.0 ml of toluene. The reaction mixture was heated at reflux temperature for approximately two and one-half hours. After cooling the resulting mixture to ambient temperature, 500.0 ml of water and 15.0 g of disodium phosphate was added. This mixture was then refluxed for approximately one-half hour and then cooled to room temperature. The toluene layer was separated and saved and the water layer discarded. The toluene layer was washed twice, each time with 400.0 ml of water, once with 400.0 ml of aqueous saturated sodium carbonate solution, then with 400.0 ml of water and finally with 400.0 ml of aqueous saturated sodium chloride solution. All of the aqueous washes were discarded. The toluene layer was then evaporated to dryness under reduced pressure. The residue was reslurried in a mixture of 200.0 ml of isopropyl alcohol, 100.0 ml of water and 20.0 g of disodium phosphate at approximately 80° C. for approximately ten minutes. After cooling, the solid was collected by filtration and dried to obtain 8.24 g of 7-(dimethylamino)-3-[N-(4-methylphenylcarbonyl)-N-methylamino]-10-(4-methylphenylcarbonyl)-phenotriazine (Formula II:$R=R^5=H$; $R^1=4-CH_3C_6H_4$; $R^2=R^3=R^4=CH_3$), a white powder which melted at 220° to 224° C. Significant infrared maxima were observed at 1670 cm$^{-1}$ (C=O;s) and 1660 cm$^{-1}$ (C=O;s). The nuclear magnetic resonance spectrum was in accord with the assigned structure. Paper treated with an ink formulation of the product produced a black-colored image when traced with an applied voltage stylus.

Proceeding in a manner similar to that described in Example 2 above, the appropriate phenothiazinium or phenoxazinium halide described in the second column of Part 1 of Table A hereinbelow was reduced in the reaction medium indicated in the third column of Part 1 with the reducing agent listed in column 4 and subsequently acylated with the acylating agent given in the fifth column of Part 1 at the temperature indicated in column 6 for the period of time specified in the seventh column of Part 1. The product obtained is given in the second column of Part 2 of Table A having the structural formula referred to in the third column of Part 2 with its physical appearance described in the fourth column of Part 2. Its melting point is shown in the fifth column of Part 2, significant infrared is shown in the sixth column of Part 2, and nuclear magnetic resonance spectral analysis is shown in the seventh column of Part 2. The color produced when a paper sheet treated with an ink formulation containing the product was traced with an applied voltage stylus is described in the eighth column of Part 2.

TABLE A

Part 1

TABLE A-continued

| Example No. | Starting Material | Reaction Medium | Reducing Agent | Acylating Agent | Temperature | Reaction Time |
|---|---|---|---|---|---|---|
| 4 | 8.0 g 7-(Dimethylamino)-3-(methylamino)phenothiazin-5-ium bromide | 100.0 ml Acetic anhydride<br>10.0 ml Pyridine | 10.0 g Zinc dust | 100.0 ml Acetic anhydride | Reflux | 0.5 Hour |
| 5 | 10.0 g 7-(Dimethylamino)-3-(methylamino)phenothiazin-5-ium chloride | 500.0 ml Water<br>500.0 ml Toluene | 10.0 g Sodium hydrosulfite | 27.6 ml 2-Naphthoic acid chloride | Reflux | 2 Hours |
| 6 | 10.0 g 7-(Dimethylamino)-3-(methylamino)-2-bromophenothiazin-5-ium chloride | 500.0 ml Water<br>500.0 ml Toluene | 10.0 g Sodium hydrosulfite | 20.0 ml Benzoyl chloride | Reflux | 2 Hours |
| 7 | 10.0 g 7-(Dimethylamino)-3-(methylamino)phenothiazin-5-ium chloride | 500.0 ml Water<br>500.0 ml Toluene | 10.0 g Sodium hydrosulfite | 20.0 g Diphenylacetyl chloride | Reflux | 2.5 Hours |
| 8 | 9.0 g 7-(Dibutylamino)-3-(methylamino)phenothiazin-5-ium chloride | 75.0 ml Acetic anhydride<br>5.0 ml Pyridine | 5.0 g Zinc dust | 75.0 ml Acetic anhydride | Reflux | 1.5 Hours |
| 9 | 6.0 g 7-(Dimethylamino)-3-(ethylamino)phenothiazin-5-ium chloride zinc chloride double salt | 80.0 ml Acetic anhydride | 4.0 g Zinc dust | 80.0 ml Acetic anhydride | Reflux | 0.5 Hour |
| 10 | 8.0 g 7-(Diethylamino)-3-(methylamino)phenothiazin-5-ium chloride zinc chloride double salt | 80.0 ml Acetic anhydride | 4.0 g Zinc dust | 80.0 ml Acetic anhydride | Reflux | 0.5 Hour |
| 11 | 8.0 g 7-(Diethylamino)-3-(methylamino)phenothiazin-5-ium chloride zinc chloride double salt | 400.0 ml Water<br>400.0 ml Toluene | 25.0 g Sodium hydrosulfite | 30.0 ml Benzoyl chloride | Reflux | 18 Hours |
| 12 | 8.0 g 7-(Dimethylamino)-3-(methylamino)phenothiazin-5-ium chloride zinc chloride double salt | 400.0 ml Water<br>400.0 ml Toluene | 25.0 g Sodium hydrosulfite | 30.0 ml Benzoyl chloride | Reflux | 19 Hours |
| 13 | 5.0 g 7-(Dimethylamino)-3-(methylamino)phenothiazin-5-ium chloride | 250.0 ml Water<br>250.0 ml Toluene | 15.0 g Sodium hydrosulfite | 10.0 g Methoxyacetyl chloride | Reflux | 2.5 Hours |
| 14 | 6.43 g 7-(N—Benzyl-N—ethylamino)-3-(methylamino)-phenothiazin-5-ium chloride | 65.0 ml Acetic anhydride | 6.5 g Zinc dust | 65.0 ml Acetic anhydride | Reflux | 0.5 Hour |
| 15 | 10.0 g 7-(Dimethylamino)-3-(methylamino)phenothiazin-5-ium chloride | 500.0 ml Water<br>500.0 ml Toluene | 10.0 g Sodium hydrosulfite | 25.0 g 2,6-Difluorobenzoyl chloride | Reflux | 2.5 Hours |

Part 2

| Example No. | Product Name | Product Formula | Physical Appearance | Melting Point | Significant Infrared | NMR | Produced Image Color |
|---|---|---|---|---|---|---|---|
| 4 | 1.85 g 7-(Dimethylamino)-3-(N—acetyl-N—methylamino)-10-acetylphenothiazine | II: $R=R^5=H$; $R^1=R^2=R^3=R^4=CH_3$ | White Powder | 147–155° C. | 1690 cm$^{-1}$ (C=O;s) | Consistent | Black |
| 5 | 0.16 g 7-(Dimethylamino)-3-(N—2-naphthylcarbonyl-N—methylamino)-10-(2-naphthylcarbonylphenothiazine | II: $R=R^5=H$; $R^1=$ 2-$C_{10}H_7$; $R^2=R^3=R^4=CH_3$ | Tan Powder | 117–122° C. | 1650 cm$^{-1}$ (C=O;s) | | Black |
| 6 | 1.39 g 7-(Dimethylamino)-3-(N—benzoyl-N—methylamino)-10-benzoylphenothiazine | II: $R=R^5=H$; $R^1=C_6H_5$; $R^2=R^3=R^4=CH_3$ | Pale Green-yellow Powder | 79–84° C. | 1655 cm$^{-1}$ (C=O;s) | | Blue-black |
| 7 | 1.3 g 7-(Dimethylamino)-3-(N—diphenylacetyl-N—methylamino)-10-diphenylacetyl phenothiazine | II: $R=R^5=H$; $R^1=$ 4-$C_4H_5C_6H_4$; $R^2=R^3=R^4=CH_3$ | Tan Powder | 78–86° C. | 1660 cm$^{-1}$ (C=O;s) | Consistent | Black |
| 8 | 0.86 g 7-(Dibutylamino)-3-(N—acetyl-N—methylamino)-10-acetylphenothiazine | II: $R=R^5=H$; $R^1=R^2=CH_3$; $R^3=R^4=C_4H_9$ | Brown Gum | — | 1670 cm$^{-1}$ (C=O;s) | | Black |
| 9 | 0.52 g 7-(Dimethylamino)-3-(N—acetyl-N—ethylamino)-10-acetylphenothiazine | II: $R=R^5=H$; $R^1=R^3=R^4=CH_3$; $R^2=C_2H_5$ | Yellow Powder | 107–110° C. | 1675 cm$^{-1}$ (C=O;s) | | Green-black |
| 10 | 1.0 g 7-(Diethylamino)-3-(N—acetyl-N—methylamino)-10-acetylphenothiazine | II: $R=R^5=H$; $R^1=R^2=CH_3$; $R^3=R^4=C_2H_5$ | Tan Powder | 92.5–97° C. | 1665 cm$^{-1}$ (C=O;s) | Consistent | Green-black |
| 11 | 1.04 g 7-(Diethylamino)-3-(N—benzoyl-N—methylamino)-10-benzoylphenothiazine | II: $R=R^5=H$; $R^1=C_6H_5$; $R^2=CH_3$; $R^3=R^4=C_2H_5$ | Brown Gum | — | 1660 cm$^{-1}$ (C=O;s) | | Black |

TABLE A-continued

| | | | | | | | | |
|---|---|---|---|---|---|---|---|---|
| 12 | 1.0 g | 7-(Dimethylamino)-3-(N—benzoyl-N—ethylamino)-10-benzoylphenothiazine | II: R=R$^5$=H; R$^1$=C$_6$H$_5$; R$^2$=C$_2$H$_5$; R$^3$=R$^4$=CH$_3$ | Brown Powder | 100–130° C. | 1650 cm$^{-1}$ (C=O;s) | | Black |
| 13 | 3.54 g | 7-(Dimethylamino)-3-(N—methoxyacetyl-N—methylamino)-10-methoxyacetyl-phenothiazine | II: R=R$^5$=H; R$^1$=CH$_3$OCH$_2$; R$^2$=R$^3$=R$^4$=CH$_3$ | Brown Gum | — | 1667 cm$^{-1}$ (C=O;s) | Consistent | Black |
| 14 | 0.52 g | 7-(N—Benzyl-N—ethylamino)-3-(N—acetyl-N—methylamino)-10-acetylphenothiazine | II: R=R$^5$=H; R$^1$=R$^2$=CH$_3$; R$^3$=C$_6$H$_5$CH$_2$; R$^4$=C$_2$H$_5$ | Brown Powder | 65–69° C. | 1670 cm$^{-1}$ (C=O;s) | | Black |
| 15 | 3.60 g | 7-(Dimethylamino)-3-[N—(2,6-difluorobenzoyl)-N—methylamino]-10-(2,6-difluorobenzoyl)-phenothiazine | II: R=R$^5$=H; R$^1$=2,6-F$_2$C$_6$H$_3$; R$^2$=R$^3$=R$^4$=CH$_3$ | Pale Brown Powder | 106–112° C. | 1670 cm$^{-1}$ (C=O;s) | | Black |

Proceeding in a manner similar to that described in Example 3 above, the appropriate phenothiazinium halide described in the second column of Part 1 of Table B hereinbelow was reduced in the reaction medium indicated in the third column of Part 1 with the reducing agent listed in column 4 and subsequently acylated with the acylating agent given in the fifth column of Part 1 at the temperature indicated in column 6 for the period of time specified in the seventh column of Part 1. The product obtained is given in the second column of Part 2 of Table B having the structural formula referred to in the third column of Part 2 with its physical appearance described in the fourth column of Part 2. Its melting point is shown in the fifth column of Part 2, significant infrared in the sixth column of Part 2, and nuclear magnetic resonance spectral analysis is shown in the seventh column of Part 2. The color produced when a paper sheet treated with an ink formulation containing the product was traced with an applied voltage stylus is described in the eighth column of Part 2.

TABLE B

Part 1

| Example No. | Starting Material | Reaction Medium | Reducing Agent | Acylating Agent | | Temperature | Reaction Time |
|---|---|---|---|---|---|---|---|
| 16 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | 4-Methylbenzoyl chloride | Reflux | 2.5 Hours |
| 17 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | 3-Nitrobenzoyl chloride | Reflux | 2 Hours |
| 18 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | Phenoxyacetyl chloride | Reflux | 2 Hours |
| 19 | 6.0 g 7-(Dimethylamino)-3-(methylamino)phenothiazin-5-ium chloride | 300.0 ml Water 300.0 ml Toluene | 12.0 g Sodium hydrosulfite | 10.0 g | 4-Bromobenzoyl chloride | Reflux | 19 Hours |
| 20 | 6.0 g 7-(Dimethylamino)-3-(methylamino)phenothiazin-5-ium chloride | 300.0 ml Water 300.0 ml Toluene | 12.0 g Sodium hydrosulfite | 10.0 g | 4-Phenylbenzoyl chloride | Reflux | 19 Hours |
| 21 | 10.0 g 7-(Dimethylamino)-3-(methylamino)phenothiazin-5-ium chloride | 500.0 ml Water 500.0 ml Toluene | 10.0 g Sodium hydrosulfite | 25.0 g | Cyclohexane carboxylic acid chloride | Reflux | 2 Hours |
| 22 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | 2-Methylbenzoyl chloride | Reflux | 2 Hours |
| 23 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | 2-Chlorobenzoyl chloride | Reflux | 2 Hours |
| 24 | 10.0 g 7-(Dimethylamino)-3-(methylamino)phenothiazin-5-ium chloride | 500.0 ml Water 500.0 ml Toluene | 10.0 g Sodium hydrosulfite | 25.0 g | 3,4,5-Trimethoxybenzoyl chloride | Reflux | 2 Hours |
| 25 | 10.0 g 7-(Dimethylamino)-3-(methylamino)phenothiazin-5-ium chloride | 500.0 ml Water 500.0 ml Toluene | 10.0 g Sodium hydrosulfite | 20.0 ml | 3-Carbomethoxypropanyl chloride | Reflux | 2 Hours |
| 26 | 5.0 g 7-(Dimethylamino)-3-(methylamino)phenothiazin-5-ium chloride | 250.0 ml Water 250.0 ml Toluene | 5.0 g Sodium hydrosulfite | 5.0 g | 4-Cyanobenzoyl chloride | Reflux | 2 Hours |
| 27 | 10.0 g 7-(Dimethylamino)-3-(methylamino)phenothiazin-5-ium chloride | 500.0 ml Water 500.0 ml Toluene | 10.0 g Sodium hydrosulfite | 25.0 ml | Decanoyl chloride | Reflux | 2 Hours |
| 28 | 13.0 g 7-(Dimethylamino)-3-(methylamino)phenothiazin-5-ium chloride | 400.0 ml Water 400.0 ml Toluene | 25.0 g Sodium hydrosulfite | 30.0 ml | Benzoyl chloride | Reflux | 4 Hours |
| 29 | 30.0 g 7-(Dimethylamino)-3-(methylamino)phenothiazin-5-ium chloride | 1500.0 ml Water 1500.0 ml Toluene | 30.0 g Sodium hydrosulfite | 50.0 ml | 4-Anisoyl chloride | Reflux | 2 Hours |
| 30 | 5.0 g 7-(Dimethylamino)-3- | 250.0 ml Water | 7.5 g Sodium | 15.0 g | 3,4-Di- | Reflux | 2 Hours |

TABLE B-continued

| | | | | | | | | |
|---|---|---|---|---|---|---|---|---|
| | | (methylamino)phenothi-azin-5-ium chloride | 300.0 ml Toluene | | hydro-sulfite | | chloro-benzoyl chloride | | |
| 31 | 10.0 g | 7-(Dimethylamino)-3-(methylamino)phenothi-azin-5-ium chloride | 500.0 ml Water 500.0 ml Toluene | 15.0 g | Sodium hydro-sulfite | 20.0 g | 2,4,6-Tri-methyl-benzoyl chloride | Reflux | 2.5 Hours |
| 32 | 10.0 g | 7-(Dimethylamino)-3-(methylamino)phenothi-azin-5-ium chloride | 500.0 ml Water 500.0 ml Toluene | 15.0 g | Sodium hydro-sulfite | 20.0 g | 2-Tri-fluorometh-ylbenzoyl chloride | Reflux | 2.5 Hours |

Part 2

| Example No. | | Product Name | Product Formula | Physical Appearance | Melting Point | Significant Infrared | NMR | Produced Image Color |
|---|---|---|---|---|---|---|---|---|
| 16 | 8.24 g | 7-(Dimethylamino)-3-[N—(4-methylphenylcarbon-yl)-N—methylamino]-10-(4-methylphenylcarbon-yl)phenothiazine | II: R = $R^5$ = H; $R^1$ = 4-$CH_3C_6H_4$; $R^2$ = $R^3$ = $R^4$ = $CH_3$ | White Powder | 220–224° C. | 1670 $cm^{-1}$ (C = O;s) 1660 $cm^{-1}$ (C = O;s) | Consistent | Black |
| 17 | 9.7 g | 7-(Dimethylamino)-3-[N—(3-nitrophenylcarbon-yl)-N—methylamino]-10-(3-nitrophenylcarbon-yl)phenothiazine | II: R = $R^5$ = H; $R^1$ = 3-$NO_2C_6H_4$; $R^2$ = $R^3$ = $R^4$ = $CH_3$ | Pale Brown Powder | 85–100° C. (dec.) | 1665 $cm^{-1}$ (C = O;s) 1650 $cm^{-1}$ (C = O;s) | | Black |
| 18 | 5.5 g | 7-(Dimethylamino)-3-(N—phenoxyacetyl-N—methyl amino)-10-phenoxyacet-ylphenothiazine | II: R = $R^5$ = H; $R^1$ = $C_6H_5OCH_2$; $R^2$ = $R^3$ = $R^4$ = $CH_3$ | White Powder | 110° C. (dec.) | 1690 $cm^{-1}$ (C = O;s) 1676 $cm^{-1}$ (C = O;s) | Consistent | Gray |
| 19 | 8.3 g | 7-(Dimethylamino)-3-[N—(4-bromophenylcarbonyl)-N—methylamino]-10-(4-bromophenylcarbonyl)-phenothiazine | II: R = $R^5$ = H; $R^1$ = 4-$BrC_6H_4$; $R^2$ = $R^3$ = $R^4$ = $CH_3$ | Pale Green Powder | 178–180° C. | 1650 $cm^{-1}$ (C = O;s) 1665 $cm^{-1}$ (C = O;s) | | Black |
| 20 | 3.1 g | 7-(Dimethylamino)-3-[N—(4-phenylphenylcarbon-yl)-N—methylamino]-10-(4-phenylphenylcarbon-yl)phenothiazine | II: R = $R^5$ = H; $R^1$ = 4-$C_6H_5C_6H_5$; $R^2$ = $R^3$ = $R^4$ = $CH_3$ | Pale Green Powder | 165–170° C. (dec.) | 1662 $cm^{-1}$ (C = O;s) 1645 $cm^{-1}$ (C = O;s) | Consistent | Black |
| 21 | 7.7 g | 7-(Dimethylamino)-3-(N—cyclohexylcarbonyl-N—methylamino)-10-cyclo-hexylcarbonylphenothi-azine | II: R = $R^5$ = H; $R^1$ = $C_6H_{11}$; $R^2$ = $R^3$ = $R^4$ = $CH_3$ | Pale Yellow Gum | — | 1662 $cm^{-1}$ (C = O;s) | | Black |
| 22 | 12.1 g | 7-(Dimethylamino)-3-[N—(2-methylphenylcarbon-yl)-N—methylamino]-10-(2-methylphenylcarbon-yl)phenothiazine | II: R = $R^5$ = H; $R^1$ = 2-$CH_3C_6H_4$; $R^2$ = $R^3$ = $R^4$ = $CH_3$ | White Powder | 211–214° C. | 1667 $cm^{-1}$ (C = O;s) 1650 $cm^{-1}$ (C = O;s) | | Black |
| 23 | 12.1 g | 7-(Dimethylamino)-3-[N—(2-chlorophenylcarbon-yl)-N—methylamino]-10-(2-chlorophenylcarbon-yl)phenothiazine | II: R = $R^5$ = H; $R^1$ = 2-$ClC_6H_9$; $R^2$ = $R^3$ = $R^4$ = $CH_3$ | White Powder | 236–243° C. | 1670 $cm^{-1}$ (C = O;s) 1652 $cm^{-1}$ (C = O;s) | | Black |
| 24 | 14.2 g | 7-(Dimethylamino)-3-[N—(3,4,5-trimethoxyphen-ylcarbonyl)-N—methyl-amino]-10-(3,4,5-tri-methylphenylcarbonyl)-phenothiazine | II: R = $R^5$ = H; $R^1$ = 3,4,5-$(CH_3O)_3C_6H_2$; $R^2$ = $R^3$ = $R^4$ = $CH_3$ | Pale Brown Powder | Tarry | 1663 $cm^{-1}$ (C = O;s) 1650 $cm^{-1}$ (C = O;s) | | Black |
| 25 | 14.2 g | 7-(Dimethylamino)-3-[N—(3-carbomethoxypropyl-carbonyl)-N—methylamino]-10-(3-carbomethoxypropyl-carbonyl)phenothiazine | II: R = $R^5$ = H; $R^1$ = 3-$CH_3OCOC_3H_6$; $R^2$ = $R^3$ = $R^4$ = $CH_3$ | Pale Yellow Gum | — | 1740 $cm^{-1}$ (C = O;s) 1665 $cm^{-1}$ (C = O;s) | | Black |
| 26 | 6.0 g | 7-(Dimethylamino)-3-[N—(4-cyanophenylcarbon-yl)-N—methylamino]-10-(4-cyanophenylcarbon-yl)phenothiazine | II: R = $R^5$ = H; $R^1$ = 4-$CNC_6H_4$; $R^2$ = $R^3$ = $R^4$ = $CH_3$ | Pale Yellow | 139–155° C. (dec.) | 1648 $cm^{-1}$ (C = O;s) 1655 $cm^{-1}$ (C = O;m) | | Black |
| 27 | 2.4 g | 7-(Dimethylamino)-3-(N—decanylcarbonyl-N—meth-ylamino)-10-decanyl-carbonylphenothiazine | II: R = $R^5$ = H; $R^1$ = $C_{10}H_{21}$; $R^2$ = $R^3$ = $R^4$ = $CH_3$ | Pale Green Tar | — | 1670 $cm^{-1}$ (C = O;s) | | Black |
| 28 | 1.84 g | 7-(Dimethylamino)-3-(N—phenylcarbonyl-N—meth-ylamino)-10-phenyl-carbonylphenothiazine | II: R = $R^5$ = H; $R^1$ = $C_6H_5$; $R^2$ = $R^3$ = $R^4$ = $CH_3$ | White Powder | 235° C. | 1670 $cm^{-1}$ (C = O;s) 1655 $cm^{-1}$ (C = O;s) | Consistent | Black |
| 29 | 26.9 g | 7-(Dimethylamino)-3-[N—(4-methoxyphenylcarbon-yl)-N—methylamino]-10- | II: R = $R^5$ = H; $R^1$ = 4-$CH_3OC_6H_4$; $R^2$ = $R^3$ = $R^4$ = $CH_3$ | White Powder | 228.5–230° C. | | (Mass Spectra and Elemental Analysis Both | Black |

TABLE B-continued

| | | (4-methoxyphenylcarbonyl)phenothiazine | | | | | (Consistent) | |
|---|---|---|---|---|---|---|---|---|
| 30 | 4.5 g | 7-(Dimethylamino)-3-[N—3,4-dichlorophenylcarbonyl)-N—methylamino]-10-(3,4-dichlorophenylcarbonyl)phenothiazine | II: R = $R^5$ = H; $R^1$ = 3,4-$ClC_6H_3$; $R^2$ = $R^3$ = $R^4$ = $CH_3$ | Yellow Powder | 223.5–225° C. | 1670 $cm^{-1}$ (C = O;s) 1645 $cm^{-1}$ (C = O;s) | Consistent | Black |
| 31 | 4.48 g | 7-(Dimethylamino)-3-[N—(2,4,6-trimethylphenylcarbonyl)-N—methylamino]-10-(2,4,6-trimethylphenylcarbonyl)phenothiazine | II: R = $R^5$ = H; $R^1$ = 2,4,6-$(CH_3)_3C_6H_2$; $R^2$ = $R^3$ = $R^4$ = $CH_3$ | Pale Green Powder | 192–194° C. | 1635 $cm^{-1}$ (C = O;s) | Consistent | Black |
| 32 | 1.02 g | 7-(Dimethylamino)-3-[N—(2-trifluoromethylphenylcarbonyl)-N—methylamino]-10-(2-trifluoromethylphenylcarbonyl)phenothiazine | II: R = $R^5$ = H; $R^1$ = $F_3CC_6H_4$; $R^2$ = $R^3$ = $R^4$ = $CH_3$ | Pale Gray | 198–210° C. | 1675 $cm^{-1}$ (C = O;s) 1663 $cm^{-1}$ (C = O;s) | | Black |

Proceeding in a manner similar to that described in Example 3 above, the appropriate phenothiazinium halide described in the second column of Part 1 of Table C hereinbelow was reduced in the reaction medium indicated in the third column of Part 1 with the reducing agent listed in column 4 and subsequently acylated with the acylating agent given in the fifth column of Part 1 at the temperature indicated in column 6 for the period of time specified in the seventh column of Part 1. The product obtained is given in the second column of Part 2 of Table C having the structural formula referred to in the third column of Part 2 with its physical appearance described in the fourth column of Part 2. Its melting point is shown in the fifth column of Part 2, significant infrared in the sixth column of Part 2, and nuclear magnetic resonance spectral analysis is shown in the seventh column of Part 2. The color produced when a paper sheet treated with an ink formulation containing the product was traced with an applied voltage stylus is described in the eighth column of Part 2.

TABLE C

Part 1

| Example No. | Starting Material | Reaction Medium | Reducing Agent | Acylating Agent | Temperature | Reaction Time |
|---|---|---|---|---|---|---|
| 33 | 10.0 g 7-(Dimethylamino)-3-methylamino)phenothiazin-5-ium chloride | 5.0 ml Pyridine 50.0 ml Hexanoic anhydride | 5.0 g Zinc dust | 50.0 ml Hexanoic anhydride | 100–110° C. | 2 Hours |
| 34 | 10.0 g 7-(Dimethylamino)-3-methylamino)phenothiazin-5-ium chloride | 5.0 ml Pyridine 50.0 ml Butyric anhydride | 5.0 g Zinc dust | 50.0 ml Butyric anhydride | 100–110° C. | 2 Hours |
| 35 | 10.0 g 7-(Dimethylamino)-3-methylamino)phenothiazin-5-ium chloride | 5.0 ml Pyridine 50.0 ml Trimethyl acetic anhydride | 5.0 g Zinc dust | 50.0 ml Trimethyl acetic anhydride | 100–105° C. | 3 Hours |
| 36 | 10.0 g 7-(Dimethylamino)-3-methylamino)phenothiazin-5-ium chloride | 5.0 ml Pyridine 100.0 ml Acetone 25.0 g Trichloroacetic anhydride | 5.0 g Zinc dust | 25.0 g Trichloroacetic anhydride | Reflux | 3 Hours |
| 37 | 10.0 g 2-Methyl-3-amino-7-dimethylaminophenothiazin-5-ium chloride | 50.0 ml Acetic Anhydride 10.0 ml Pyridine | 10.0 g Zinc dust | 50.0 ml Acetic Anhydride | 85–90° C. | 1 Hour |
| 38 | 15.0 g 2-Methyl-3-amino-7-dimethylaminophenothiazin-5-ium chloride | 400.0 ml Water 400.0 ml Toluene | 40.0 g Sodium Hydrosulfite | 20.0 ml Benzoyl Chloride | 60–65° C. | 1 Hour |
| 39 | 10.0 g 2-Methyl-3-amino-7-dimethylaminophenothiazin-5-ium chloride | 400.0 ml Water 400.0 ml Toluene | 30.0 g Sodium Hydrosulfite | 25.0 ml Anisoyl Chloride | Reflux | 2.5 Hours |
| 40 | 10.0 g 2-Methyl-3-amino-7-dimethylaminophenothiazin-5-ium chloride | 75.0 ml Butyric Anhydride 10.0 ml Pyridine | 6.0 g Zinc Dust | 75.0 ml Butyric Anhydride | 70° C. | 4 Hours |

Part 2

| Example No. | Product Name | Product Formula | Physical Appearance | Melting Point | Significant Infrared | NMR | Produced Image Color |
|---|---|---|---|---|---|---|---|
| 33 | 31.57 g 7-(Dimethylamino)-3-(N—hexanoyl-N—methylamino)-10-hexanoylphenothiazine | II: R = $R^5$ = H; $R^1$ = $C_6H_{13}$; $R^2$ = $R^3$ = $R^4$ = $CH_3$ | Brown Gummy Solid | — | 1670 $cm^{-1}$ (C = O;s) | Consistent | Black |
| 34 | 24.4 g 7-(Dimethylamino)-3-(N—butyryl-N—methylamino)-10-butyrylphenothiazine | II: R = $R^5$ = H; $R^1$ = $C_4H_9$; $R^2$ = $R^3$ = $R^4$ = $CH_3$ | Orange-brown Gummy | — | 1660 $cm^{-1}$ (C = O;s) | Consistent | Black |

TABLE C-continued

| | | | | | | | | |
|---|---|---|---|---|---|---|---|---|
| 35 | 5.49 g | 7-(Dimethylamino)-3-(N—trimethylacetyl-N—methylamino)-10-trimethylacetylphenothiazine | II: R = R$^5$ = H; R$^1$ = (CH$_3$)$_3$C; R$^2$ = R$^3$ = R$^4$ = CH$_3$ | Solid Dark Green Powder | 174–180° C. | 1620 cm$^{-1}$ (C = O;s) | | |
| 36 | 5.9 g | 7-(Dimethylamino)-3-(N—trichloroacetyl-N—methylamino)-10-trichloroacetylphenothiazine | II: R = R$^5$ = H; R$^1$ = Cl$_3$C; R$^2$ = R$^3$ = R$^4$ = CH$_3$ | Blue Powder | 280–285° C. | 1675 cm$^{-1}$ (C = O;s) | | |
| 37 | 0.95 g | 2-Methyl-3-acetamido-7-dimethylamino-10-acetylphenothiazine | II: R = 2-CH$_3$; R$^1$ = R$^3$ = R$^4$ = CH$_3$; R$^2$ = H | Tan Powder | 157–159° C. | 1668 cm$^{-1}$ (C = O;s) | Consistent (Mass Spec. Consistent) | Gray |
| 38 | 1.8 g | 2-Methyl-3-benzamido-7-dimethylamino-10-benzoylphenothiazine | II: R = 2-CH$_3$; R$^1$ = C$_6$H$_5$; R$^2$ = H; R$^3$ = R$^4$ = CH$_3$ | Yellow Powder | 167–175° C. | 1650 cm$^{-1}$ (C = O;s) | | Gray |
| 39 | 2.65 g | 2-Methyl-3-(4-methylphenylamido)-7-dimethylamino-10-(4-methylphenylcarbonyl)phenothiazine | II: R = 2-CH$_3$; R$^1$ = 4-CH$_3$C$_6$H$_4$; R$^2$ = H; R$^3$ = R$^4$ = CH$_3$ | Pale Yellow Powder | 238–242° C. | 1650 cm$^{-1}$ (C = O;s) | | Blue-gray |
| 40 | 1.46 g | 2-Methyl-3-butyrylamido-7-dimethylamino-10-butyrylcarbonylphenothiazine | II: R = 2-CH$_3$; R$^1$ = C$_3$H$_7$; R$^2$ = H; R$^3$ = R$^4$ = CH$_3$ | White Powder | 208–210° C. | 1665 cm$^{-1}$ (C = O;s) | Consistent | Blue-gray |

It is contemplated that by following the procedure described in the foregoing examples, but employing the appropriate 1/2-R-3-(N-R$^2$-amino)-7-(N-R$^3$-N-R$^4$-amino)phenothiazinium halide or phenoxazinium halide of Formula IV with a reducing agent and the appropriate acid halide of Formula VII or alkanoic acid anhydride of Formula VI, there will be obtained 1/2-R-3-(N-R$^2$-N-COR$^1$-amino)-7-(N-R$^3$-N-R$^4$-amino)-10-(R$^1$-CO)-phenothiazine or phenoxazine of Formula I, presented in Examples 41 to 59 in Table D hereinbelow.

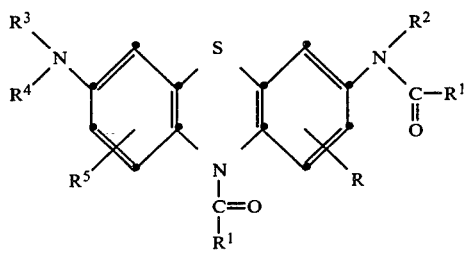

TABLE D

| Example No. | R | R$^1$ | R$^2$ | R$^3$ | R$^4$ | R$^5$ |
|---|---|---|---|---|---|---|
| 41 | C$_2$H$_5$O | ClCH$_2$ | CH$_3$ | C$_6$H$_5$CH$_2$ | C$_6$H$_5$CH$_2$ | H |
| 42 | Cl | CH$_3$OCH$_2$ | C$_2$H$_5$ | C$_2$H$_5$ | CH$_3$ | CH$_3$ |
| 43 | C$_2$H$_5$ | C$_3$H$_5$ | C$_4$H$_9$ | C$_6$H$_5$ | CH$_3$ | CH$_3$O |
| 44 | Br | Cl$_2$CH | CH$_3$ | C$_4$H$_9$ | C$_4$H$_9$ | H |
| 45 | NO$_2$ | C$_5$H$_{11}$ | C$_3$H$_7$ | 4-CH$_3$C$_6$H$_4$CH$_2$ | 4-CH$_3$C$_6$H$_4$CH$_2$ | Br |
| 46 | C$_4$H$_9$O | BrCH$_2$ | CH$_3$ | 4-NO$_2$C$_6$H$_4$CH$_2$ | CH$_3$ | NO$_2$ |
| 47 | H | 3-BrC$_2$H$_4$ | C$_6$H$_4$CH$_2$ | CH$_3$ | C$_6$H$_5$ | C$_4$H$_9$ |
| 48 | CH$_3$ | 2-BrC$_2$H$_4$ | CH$_3$ | 3-ClC$_6$H$_4$CH$_2$ | C$_2$H$_5$ | CH$_3$ |
| 49 | CH$_3$O | 3-ClC$_3$H$_6$ | C$_4$H$_9$ | C$_4$H$_9$ | C$_4$H$_9$ | C$_2$H$_5$O |
| 50 | F | 2-(C$_2$H$_5$)C$_3$H$_6$ | CH$_3$ | C$_2$H$_5$ | 3-BrC$_6$H$_4$CH$_2$ | C$_3$H$_7$ |
| 51 | NO$_2$ | 5-BrC$_5$H$_{10}$ | C$_2$H$_5$ | 2,4-Cl$_2$C$_6$H$_3$CH$_2$ | CH$_3$ | F |
| 52 | C$_3$H$_7$ | C$_{11}$H$_{23}$ | CH$_3$ | C$_2$H$_5$ | 2,3-(CH$_3$)$_2$C$_6$H$_3$CH$_2$ | NO$_2$ |
| 53 | C$_2$H$_5$O | C$_3$H$_5$ | C$_3$H$_7$ | 2,5-(CH$_3$)$_2$C$_6$H$_3$CH$_2$ | C$_2$H$_5$ | CH$_3$ |
| 54 | I | 4-C$_4$H$_9$OC$_6$H$_4$ | CH$_3$ | 2,6-Cl$_2$C$_6$H$_3$CH$_2$ | CH$_3$ | H |
| 55 | H | 4-C$_4$H$_9$C$_6$H$_4$ | C$_6$H$_5$ | 2-FC$_6$H$_4$CH$_2$ | C$_4$H$_9$ | C$_4$H$_9$O |
| 56 | CH$_3$ | 2,4-Cl$_2$C$_6$H$_3$ | CH$_3$ | 2-CH$_3$C$_6$H$_4$CH$_2$ | 2-CH$_3$C$_6$H$_4$CH$_2$ | H |
| 57 | CH$_3$O | 3,5-(CH$_3$O)$_2$C$_6$H$_3$ | 4-CH$_3$C$_6$H$_4$CH$_2$ | 4-CH$_3$C$_6$H$_4$CH$_2$ | C$_2$H$_5$ | Br |
| 58 | Cl | 3,5-(NO$_2$)$_2$C$_6$H$_3$ | 4-ClC$_6$H$_4$CH$_2$ | C$_2$H$_5$ | C$_2$H$_5$ | C$_2$H$_5$ |
| 59 | NO$_2$ | 2-IC$_6$H$_4$ | 3-NO$_2$C$_6$H$_4$CH$_2$ | CH$_3$ | CH$_3$ | C$_4$H$_9$ |

What is claimed is:

1. A substrate for use in electrochromic recording comprising a support sheet containing as a color-forming substance a 1/2-R-3-[N(R$^1$-CO)-N-R$^2$-amino]-7-[N-(R$^3$)(R$^4$)-amino]-8/9-R$^5$-10-(R$^1$-CO)-phenothiazine having the formula wherein:

R and R$^5$ independently represent hydrogen, non-tertiary C$_1$ to C$_4$ alkyl, non-tertiary C$_1$ to C$_4$ alkoxy, halogen or nitro;

R$^1$ represents hydrogen, non-tertiary C$_1$ to C$_{12}$ alkyl, C$_4$ to C$_8$ cycloalkyl, non-tertiary C$_1$ to C$_4$ alkoxy or non-tertiary C$_1$ to C$_4$ alkoxycarbonyl, phenyl, phenyl substituted by one to three of non-tertiary C$_1$ to C$_4$ alkyl, non-tertiary C$_1$ to C$_4$ alkoxy, nitro, halo, phenyl, cyano, or trihalomethyl;

R$^2$ represents C$_1$ to C$_4$ alkyl, phenyl, phenyl substituted by one or two of halo, nitro, non-tertiary C$_1$ to C$_4$ alkyl or non-tertiary C$_1$ to C$_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; and $R^3$ and $R^4$ independently represent $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy.

2. A substrate for use in electrochromic recording according to claim 1 comprising a support sheet containing as a color-forming substance 3-(N-acetyl-N-methylamino)-7-(dimethylamino)-10-acetylphenothiazine.

3. A substrate for use in electrochromic recording according to claim 1 comprising a support sheet containing as a color-forming substance 3-[N-(4-methoxyphenylcarbonyl)-N-methylamino]-7-(dimethylamino)-10-(4-methoxyphenylcarbonyl)phenothiazine.

4. A substrate for use in electrochromic recording according to claim 1 comprising a support sheet containing as a color-forming substance 3-(N-propylcarbonyl-N-methylamino)-7-(dimethylamino)-10-propylcarbonylphenothiazine.

5. A substrate for use in electrochromic recording according to claim 1 comprising a support sheet containing as a color-forming substance 3-[N-(4-methylphenylcarbonyl)-N-methylamino]-7-(diethylamino)-10-(4-methylphenylcarbonyl)-phenothiazine.

6. A substrate for use in electrochromic recording according to claim 1 comprising a support sheet containing as a color-forming substance 2-methyl-3-(N-acetyl-N-methylamino)-7-(dimethylamino)-10-acetylphenothiazine.

7. A substrate for use in electrochromic recording according to claim 1 comprising a support sheet containing as a color-forming substance 3-(N-acetyl-N-methylamino)-7-(dibutylamino)-10-acetylphenothiazine.

8. A substrate for use in electrochromic recording comprising a support sheet containing as a color-forming substance a 1/2-R-3-[N-($R^1$-CO)-N-$R^2$-amino]-7-[N-($R^3$)($R^4$)-amino]-8/9-$R^5$-10-($R^1$-CO)-phenoxazine having the formula

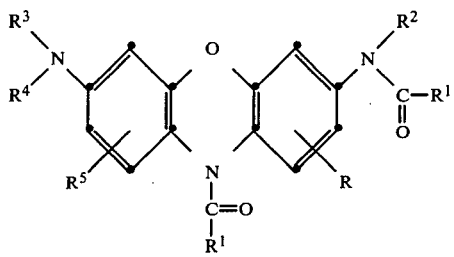

wherein:

R and $R^5$ independently represent hydrogen, non-tertiary $C_1$ to $C_4$ alkyl, non-tertiary $C_1$ to $C_4$ alkoxy, halogen or nitro;

$R^1$ represents hydrogen, non-tertiary $C_1$ to $C_{12}$ alkyl, $C_4$ to $C_8$ cycloalkyl, non-tertiary $C_1$ to $C_4$ alkoxy or non-tertiary $C_1$ to $C_4$ alkoxycarbonyl, phenyl, phenyl substituted by one to three of non-tertiary $C_1$ to $C_4$ alkyl, non-tertiary $C_1$ to $C_4$ alkoxy, nitro, halo, phenyl, cyano, or trihalomethyl;

$R^2$ represents $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; and $R^3$ and $R^4$ independently represent $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy.

* * * * *